United States Patent
Daum et al.

(10) Patent No.: US 7,101,339 B2
(45) Date of Patent: Sep. 5, 2006

(54) RESPIRATION SIGNAL MEASUREMENT APPARATUS, SYSTEMS, AND METHODS

(75) Inventors: Douglas R. Daum, Oakdale, MN (US); Qingsheng Zhu, Little Canada, MN (US); Avram Scheiner, Vadnais Heights, MN (US)

(73) Assignee: Cardiac Pacemakers, Inc., Saint Paul, MN (US)

(*) Notice: Subject to any disclaimer, the term of this patent is extended or adjusted under 35 U.S.C. 154(b) by 559 days.

(21) Appl. No.: 10/319,794

(22) Filed: Dec. 13, 2002

(65) Prior Publication Data

US 2004/0116820 A1 Jun. 17, 2004

(51) Int. Cl.
*A61B 5/08* (2006.01)

(52) U.S. Cl. ........................ 600/529; 600/508

(58) Field of Classification Search .................. 607/42
See application file for complete search history.

(56) References Cited

U.S. PATENT DOCUMENTS

| | | | |
|---|---|---|---|
| 3,593,718 A | 7/1971 | Krasner | |
| 4,009,721 A | 3/1977 | Alcidi | |
| 4,140,132 A | 2/1979 | Dahl | |
| 4,228,803 A | 10/1980 | Rickards | |
| 4,291,699 A | 9/1981 | Geddes et al. | |
| 4,399,820 A | 8/1983 | Wirtzfeld et al. | |
| 4,428,378 A | 1/1984 | Anderson et al. | |
| 4,510,944 A | 4/1985 | Porges | 128/687 |
| 4,519,395 A | 5/1985 | Hrushesky | 128/671 |
| 4,543,954 A | 10/1985 | Cook et al. | |
| 4,562,843 A | 1/1986 | Djordjevich et al. | |
| 4,596,251 A | 6/1986 | Plicchi et al. | |
| 4,686,987 A | 8/1987 | Salo et al. | |
| 4,702,253 A | 10/1987 | Nappholz et al. | |
| 4,722,351 A | 2/1988 | Phillipps et al. | |
| 4,773,401 A | 9/1988 | Citak et al. | |
| 4,781,201 A | 11/1988 | Wright et al. | |
| 4,858,611 A | 8/1989 | Elliott | |
| 4,899,752 A | 2/1990 | Cohen | |
| 4,901,725 A | 2/1990 | Nappholz et al. | |

(Continued)

FOREIGN PATENT DOCUMENTS

DE 2805482 3/1987

(Continued)

OTHER PUBLICATIONS

"BioZ(r) ICG Module", http://web.archive.org/web/20010701105207/http://www.cardiodynamics.com/cdprod50.html (archived on Jul. 1, 2001), 1 page.

(Continued)

*Primary Examiner*—Robert L. Nasser
*Assistant Examiner*—Patricia C. Mallari
(74) *Attorney, Agent, or Firm*—Schwegman, Lundberg, Woessner & Kluth, P.A.

(57) ABSTRACT

A cardiac rhythm management apparatus and system may include a first sensor to sense an atrial respiration signal, a second sensor to sense a ventricular respiration signal, and a measurement module capable of being communicatively coupled to the first and second sensors to monitor the atrial and ventricular respiration signals and to select a resulting signal as an indication of respiration. An article may cause a machine to implement a method which includes measuring a second signal responsive to a first signal, measuring a third signal responsive to a first signal, determining a respiration-to-cardiac ratio associated with each one of the second and third signals, and providing a resulting signal including a selected portion of a selected one of the second and third signals as an indication of respiration.

24 Claims, 2 Drawing Sheets

U.S. PATENT DOCUMENTS

| | | | |
|---|---|---|---|
| 4,930,518 A | 6/1990 | Hrushesky | 128/671 |
| 4,960,129 A | 10/1990 | dePaola et al. | 128/695 |
| 4,966,146 A | 10/1990 | Webb et al. | |
| 5,003,976 A | 4/1991 | Alt | |
| 5,014,698 A | 5/1991 | Cohen | |
| 5,027,813 A | 7/1991 | Pederson et al. | |
| 5,063,927 A | 11/1991 | Webb et al. | |
| 5,074,303 A | 12/1991 | Hauck | |
| 5,085,215 A | 2/1992 | Nappholz et al. | |
| 5,105,819 A | 4/1992 | Wollschlager et al. | |
| 5,107,850 A | 4/1992 | Olive | |
| 5,137,019 A | 8/1992 | Pederson et al. | |
| 5,156,147 A | 10/1992 | Warren et al. | |
| 5,174,286 A | 12/1992 | Chirife | |
| 5,179,946 A | 1/1993 | Weiss | |
| 5,190,035 A | 3/1993 | Salo et al. | |
| 5,197,467 A | 3/1993 | Steinhaus et al. | |
| 5,201,808 A | 4/1993 | Steinhaus et al. | |
| 5,203,326 A | 4/1993 | Collins | |
| 5,235,237 A | 8/1993 | Leonhardt | |
| 5,235,976 A | 8/1993 | Spinelli | |
| 5,249,572 A | 10/1993 | Bonnet | |
| 5,269,301 A | 12/1993 | Cohen | |
| 5,271,395 A | 12/1993 | Wahlstrand et al. | |
| 5,273,034 A | 12/1993 | Nilsson | |
| 5,284,136 A | 2/1994 | Hauck et al. | |
| 5,300,093 A | 4/1994 | Koestner et al. | |
| 5,303,702 A | 4/1994 | Bonnet et al. | |
| 5,314,449 A | 5/1994 | Lindgren | 607/24 |
| 5,318,597 A | 6/1994 | Hauck et al. | |
| 5,341,811 A | 8/1994 | Cano | |
| 5,354,317 A | 10/1994 | Alt | |
| 5,379,776 A | 1/1995 | Murphy et al. | |
| 5,383,473 A | 1/1995 | Moberg | |
| 5,391,190 A | 2/1995 | Pederson et al. | |
| 5,423,870 A | 6/1995 | Olive et al. | |
| 5,423,883 A | 6/1995 | Helland | |
| 5,431,687 A | 7/1995 | Kroll | 607/8 |
| 5,431,693 A | 7/1995 | Schroeppel | |
| 5,437,285 A | 8/1995 | Verrier et al. | |
| 5,441,524 A | 8/1995 | Rueter et al. | |
| 5,466,245 A | 11/1995 | Spinelli et al. | 607/17 |
| 5,469,859 A | 11/1995 | Tsoglin et al. | |
| 5,480,412 A | 1/1996 | Mouchawar et al. | |
| 5,490,323 A | 2/1996 | Thacker et al. | |
| 5,501,702 A | 3/1996 | Plicchi et al. | 607/20 |
| 5,507,785 A | 4/1996 | Deno | |
| 5,511,554 A | 4/1996 | Helfenbein et al. | |
| 5,522,860 A | 6/1996 | Molin et al. | |
| 5,524,632 A | 6/1996 | Stein et al. | |
| 5,531,772 A | 7/1996 | Prutchi | |
| 5,560,370 A | 10/1996 | Verrier et al. | |
| 5,562,711 A | 10/1996 | Yerich et al. | |
| 5,562,712 A | 10/1996 | Steinhaus et al. | |
| 5,626,622 A | 5/1997 | Cooper | |
| 5,626,624 A | 5/1997 | Schaldach et al. | 607/24 |
| 5,685,316 A | 11/1997 | Schookin et al. | |
| 5,700,283 A | 12/1997 | Salo | |
| 5,713,933 A | 2/1998 | Condie et al. | 607/28 |
| 5,718,235 A | 2/1998 | Golosarsky et al. | 128/708 |
| 5,718,720 A | 2/1998 | Prutchi et al. | |
| 5,722,997 A | 3/1998 | Nedungadi et al. | |
| 5,749,900 A | 5/1998 | Schroeppel et al. | 607/4 |
| 5,755,671 A | 5/1998 | Albrecht et al. | |
| 5,766,225 A | 6/1998 | Kramm | |
| 5,782,884 A | 7/1998 | Stotts et al. | |
| 5,792,194 A | 8/1998 | Morra | 607/17 |
| 5,800,470 A | 9/1998 | Stein et al. | |
| 5,817,135 A | 10/1998 | Cooper et al. | |
| 5,817,136 A | 10/1998 | Nappholz et al. | |
| 5,824,020 A | 10/1998 | Cooper | |
| 5,824,029 A | 10/1998 | Weijand et al. | |
| 5,836,975 A | 11/1998 | DeGroot | 607/5 |
| 5,836,976 A | 11/1998 | Min et al. | 607/6 |
| 5,836,987 A | 11/1998 | Baumann et al. | |
| 5,842,997 A | 12/1998 | Verrier et al. | |
| 5,873,897 A | 2/1999 | Armstrong et al. | |
| 5,876,353 A | 3/1999 | Riff | |
| 5,891,044 A | 4/1999 | Golosarsky et al. | 600/509 |
| 5,921,940 A | 7/1999 | Verrier et al. | |
| 5,935,081 A | 8/1999 | Kadhiresan | |
| 5,957,861 A | 9/1999 | Combs et al. | |
| 5,974,340 A * | 10/1999 | Kadhiresan | 607/18 |
| 5,978,707 A | 11/1999 | Krig et al. | |
| 5,978,710 A | 11/1999 | Prutchi et al. | |
| 5,987,356 A | 11/1999 | DeGroot | |
| 6,006,134 A | 12/1999 | Hill et al. | |
| 6,015,388 A | 1/2000 | Sackner et al. | |
| 6,021,351 A | 2/2000 | Kadhiresan et al. | |
| 6,022,322 A | 2/2000 | Prutchi | |
| 6,026,320 A | 2/2000 | Carlson et al. | |
| 6,035,233 A | 3/2000 | Schroeppel et al. | |
| 6,042,548 A | 3/2000 | Giuffre | |
| 6,044,294 A | 3/2000 | Mortazavi et al. | |
| 6,049,735 A | 4/2000 | Hartley et al. | |
| 6,058,331 A | 5/2000 | King | |
| 6,073,048 A | 6/2000 | Kieval et al. | |
| 6,076,015 A | 6/2000 | Hartley et al. | |
| 6,135,970 A | 10/2000 | Kadhiresan et al. | |
| 6,144,878 A | 11/2000 | Schroeppel et al. | |
| 6,151,524 A | 11/2000 | Krig et al. | |
| 6,161,042 A | 12/2000 | Hartley et al. | |
| 6,179,865 B1 | 1/2001 | Hsu et al. | |
| 6,193,668 B1 | 2/2001 | Chassaing et al. | |
| 6,212,428 B1 | 4/2001 | Hsu et al. | |
| 6,223,064 B1 | 4/2001 | Lynn et al. | |
| 6,272,377 B1 | 8/2001 | Sweeney et al. | |
| 6,275,727 B1 | 8/2001 | Hopper et al. | |
| 6,317,632 B1 | 11/2001 | Krig et al. | |
| 6,358,201 B1 | 3/2002 | Childre et al. | |
| 6,370,424 B1 | 4/2002 | Prutchi | |
| 6,371,922 B1 | 4/2002 | Baumann et al. | |
| 6,390,986 B1 | 5/2002 | Curcie et al. | |
| 6,411,840 B1 | 6/2002 | Bardy | |
| 6,415,183 B1 | 7/2002 | Scheiner et al. | |
| 6,430,435 B1 | 8/2002 | Hsu et al. | |
| 6,456,871 B1 | 9/2002 | Hsu et al. | |
| 6,459,929 B1 | 10/2002 | Hopper et al. | |
| 6,463,326 B1 | 10/2002 | Hartley et al. | |
| 6,473,644 B1 | 10/2002 | Terry, Jr. et al. | |
| 6,478,746 B1 | 11/2002 | Chassaing et al. | |
| 6,480,733 B1 | 11/2002 | Turcott | |
| 6,484,055 B1 | 11/2002 | Marcovecchio | |
| 6,511,500 B1 | 1/2003 | Rahme | |
| 6,512,940 B1 | 1/2003 | Brabec et al. | |
| 6,520,924 B1 | 2/2003 | Lee | |
| 6,522,914 B1 * | 2/2003 | Huvelle et al. | 600/509 |
| 6,522,917 B1 | 2/2003 | Hsu et al. | |
| 6,522,925 B1 | 2/2003 | Gilkerson et al. | |
| 6,522,926 B1 | 2/2003 | Kieval et al. | |
| 6,526,313 B1 | 2/2003 | Sweeney et al. | |
| 6,529,772 B1 | 3/2003 | Carlson et al. | |
| 6,561,986 B1 | 5/2003 | Baura et al. | |
| 6,571,121 B1 | 5/2003 | Schroeppel et al. | |
| 6,571,122 B1 | 5/2003 | Schroeppel et al. | |
| 6,574,506 B1 | 6/2003 | Kramer et al. | |
| 6,575,916 B1 | 6/2003 | Halleck et al. | |
| 6,589,188 B1 | 7/2003 | Street et al. | |
| 6,611,713 B1 | 8/2003 | Schauerte | |
| 6,647,289 B1 | 11/2003 | Prutchi | |
| 6,687,540 B1 | 2/2004 | Marcovecchio | |
| 6,690,971 B1 | 2/2004 | Schauerte et al. | |
| 6,868,346 B1 | 3/2005 | Larson et al. | |
| 2002/0002389 A1 * | 1/2002 | Bradley et al. | 607/8 |

| | | | |
|---|---|---|---|
| 2002/0026222 A1 | 2/2002 | Schauerte et al. | |
| 2002/0049474 A1 | 4/2002 | Marcovecchio et al. | |
| 2002/0058877 A1 | 5/2002 | Baumann et al. | |
| 2002/0107552 A1 | 8/2002 | Krig et al. | |
| 2002/0107553 A1 | 8/2002 | Hill et al. | |
| 2002/0123768 A1 | 9/2002 | Gilkerson | |
| 2002/0123769 A1 | 9/2002 | Panken et al. | |
| 2002/0198461 A1 | 12/2002 | Hsu et sl. | |
| 2003/0032991 A1 | 2/2003 | Poore | |
| 2003/0055461 A1 | 3/2003 | Girouard et al. | |
| 2003/0060849 A1 | 3/2003 | Hsu | |
| 2003/0069609 A1 | 4/2003 | Thompson | |
| 2003/0105491 A1 | 6/2003 | Gilkerson et al. | |
| 2003/0105499 A1 | 6/2003 | Hartley et al. | |
| 2003/0109792 A1 | 6/2003 | Hsu et al. | |
| 2003/0114889 A1 | 6/2003 | Huvelle et al. | |
| 2003/0120316 A1 | 6/2003 | Spinelli et al. | |
| 2003/0191503 A1 | 10/2003 | Zhu et al. | |
| 2003/0216664 A1 | 11/2003 | Suarez | |
| 2004/0015090 A1 | 1/2004 | Sweeney et al. | |
| 2004/0039295 A1 | 2/2004 | Olbrich et al. | |
| 2004/0049237 A1 | 3/2004 | Larson et al. | |
| 2004/0093035 A1 | 5/2004 | Schwartz et al. | |
| 2004/0102712 A1 | 5/2004 | Belalcazar et al. | |
| 2004/0116820 A1 | 6/2004 | Daum et al. | |
| 2004/0116972 A1 | 6/2004 | Marcovecchio | |
| 2005/0004609 A1 | 1/2005 | Stahmann et al. | |
| 2005/0004610 A1 | 1/2005 | Kim et al. | |
| 2005/0096704 A1 | 5/2005 | Freeberg | |
| 2005/0149135 A1 | 7/2005 | Krig et al. | |
| 2005/0159781 A1 | 7/2005 | Hsu et al. | |
| 2005/0197674 A1 | 9/2005 | McCabe et al. | |
| 2006/0020295 A1 | 1/2006 | Brockway et al. | |

FOREIGN PATENT DOCUMENTS

| | | |
|---|---|---|
| EP | 0003567 A1 | 8/1979 |
| EP | 0360412 A1 | 3/1990 |
| EP | 0401962 A2 | 12/1990 |
| EP | 0447024 A2 | 9/1991 |
| EP | 0555988 A2 | 8/1993 |
| EP | 0597459 A2 | 5/1994 |
| EP | 0617980 A2 | 10/1994 |
| EP | 0709058 A1 | 1/1996 |
| EP | 0702977 A2 | 3/1996 |
| EP | 0744190 A2 | 11/1996 |
| EP | 0748638 A2 | 12/1996 |
| EP | 765632 A2 | 4/1997 |
| WO | WO-93/02746 A1 | 6/1992 |
| WO | WO-94/06512 A1 | 3/1994 |
| WO | WO-98/14240 A1 | 4/1998 |
| WO | WO-9943385 | 9/1999 |
| WO | WO-00/44274 | 8/2000 |
| WO | WO-00744775 A1 | 12/2000 |
| WO | WO-03077759 A1 | 9/2003 |

OTHER PUBLICATIONS

"BioZ.com(tm) Noninvasive Hemodynamic Monitor", http://web/archive.org/web/20000617081457/http://www.cardiodynamics.com/cdprod10.html (archived Jun. 17, 2000), 2 pages.

"CardioDynamics BioZtect ICG Sensor & Cable System", http://web.archive.org/web/200107011105810/http://www.cardiodynamics.com/cdprod60.html, (archived Jul. 1, 2001),2 pages.

"CardioDynamics Company Overview", http://web.archive.org/web/20001121133300/http://www.cardiodynamics.com/cdcomp10.html, (archived Nov. 21, 2000),2 pages.

"Overview of Impedance Cardiography (ICG)", http:/web.archive.org/web/20021003000713/http://www.impedancecariography.com/icgover10.html, (archived Oct. 3, 2002),5 pages.

Alt, Eckhard , "What is the Ideal Rate-Adaptive Sensor for Patients with Implantable Cardioverter Defibrillators: Lessons from Cardiac Pacing", *American Journal of Cardiology*, 83(5B), (Mar. 11, 1999),17D-23D.

Barold, S. , et al., "Contemporary issues in rate-adaptive pacing", *Clin. Cardiol.*, 20(8), (Aug. 1997),726-729.

Brockway, Marina, et al., "Method And Apparatus for Monitoring Heart Failure Patients With Cardiopulmonary Comorbidites", U.S. Appl. No. 10/897,856, filed Jul. 23, 2004, 54 pages.

Euler, D. E., et al., "Inspiration Induced by Phrenic Nerve Stimulation Increases Defribillation Energy Requirements", *PACE(22), Part II, Abstract No. 307*, (1999),777.

Freeberg, S. , "Cross-Checking of Transthoracic Impedance and Acceleration Signals", U.S. Appl. No. 10/696,729, filed Oct. 29, 2003, 27 pages.

Hauck, John A., "A Minute Ventilation Sensor Derived from Intrathoracic Electric Impedance as a Cardiac Pacemaker Rate Modulator", *University of Minnesota Master Thesis*, (Jun. 1993),pp. 80-86 & 97.

Hayano, J. , et al., "Resporatory Sinus Arrhythmia: a Phenomenon Improving Pulmonary Gas Exchange and Circulatory Efficiency", *Circulation*, 94(4), (1996), 842-847.

Hsu, William, "System and Method for Classifying Tachycardia Arrhythmias Having 1:1 Atrial to Ventricular Rhythms", U.S. Appl. No. 09/417,588, filed Oct. 13, 1999, 39 pages.

Jackson, LeLand B., "Chapter 11 / Quantization Effects", *Digital Filters and Signal Processing*, 2d Edition, Kluwer Academic Publishers,(1989),pp. 297-340.

Johnston, P. W., et al., "The Transthoracic Impedance Cardiogram is a Potential Haemodynamic Sensor for an Automated External Defibrillator", *European Heart Journal*, 19(12), (Dec. 1998),1879-1888.

Kim, J. , et al., "Cardiac Cycle Synchronized Sampling of Impedance Signal", U.S. Appl. No. 10/612,388, filed Jul. 2, 2003, 28 pages.

Lincoln, William C., "Classifying Tachyarrhythmia Using Time Interval Between Ventricular Depolarization and Mitral Valve Closure", U.S. Appl. No. 10/618,261, filed Jul. 11, 2003, 26 pages.

Ponikowski, P. , et al., "Oscillatory Implications and Role of Augmented Peripheral Chemosensitivity", *Circulation*, 100, (1999),2418-2424.

Rickards, Anthony , et al., "An Implantable Intracardiac Accelerometer for Monitoring Myocardial Contractility." *Pacing Clin Electrophysiol.*, 19(12 Pt 1), (Dec. 1996), 2066-2071.

Ruiter, J H., et al., "Adaptive Rate Pacing Controlled by the Right Ventricular Preejection Interval: Clinical Experience with a Physiological Pacing System", *Pacing Clin Electrophysiol.*, 15(6), (Jun. 1992),886-94.

Salo, Rodney W., et al., "Continuous Ventricular Volume Assessment for Diagnosis and Pacemaker Control", *Pacing Clin Electrophysiol.*, 7(6 Pt 2), (Nov. 1984),1267-1272.

Salo, Rodney W., "Measurement of Ventricular Volume by Intracardiac Impedance: Theoretical and Empirical Approaches", *IEEE Transactions on Biomedical Engineering*, 33(2), (Feb. 1986),189-195.

Salo, R W., "The Theoretical Basis of a Computational Model for the Determination of Volume by Impedence", *Automedica*, 11, (1989),299-310.

Schaldach, M., "Automatic Adjustment of Pacing Parameters Based on Intracardiac Impedance Measurements", *Pacing Clin Electrophysiol.*, 13(12) (Pt 2), (Dec. 1990),1702-1710.

Schaldach, M., et al., "Intracardiac Impedance to Determine Sympathetic Activity in Rate Responsive Pacing", *Pacing Clin Electrophysiol.*, 15(11) (Pt 2), (Nov. 1992), 1778-1786.

Stahmann, J. E., et al., "Implantable Devices and Methods Using Frequency-Domain Analysis of Thoracic Signal", U.S. Appl. No. 10/612,387, filed Jul. 2, 2003, 39 pages.

Sweeney, R. J., et al., "Device for Monitoring Fluid Status", U.S. Appl. No. 10/909,926, filed Aug. 2, 2004, 17 pages.

Zhang, Y. , et al., "Method and Apparatus for Arrhythmia Detection and Discrimination Using Wireless ECG", *Unassigned Serial Number, filed Oct. 28, 2004*, 69 pages.

"Heart Rate Variability: Standards of Measurement, Physiological Interpretation, and Clinical Use", *European Heart Journal*, 17, Prepared by the Task Force of The European Society of Cardiology and The North American Society of Pacing and Electrophysiology;

published by the American Heart Association, Inc.; European Society of Cardiology,(1996),pp. 354-381.

Behrens, S. , "Effects of Amiodarone on the Circadian Pattern of Sudden Cardiac Death (Department of Vererans Affairs Congestive Heart Failure-Survival Trial of Antiarrhythmic Therapy)", *Am. J. Cardiol.*, 80(1) (Jul. 1997),45-48.

Behrens, S. , "Modification of the Circadian Pattern of Ventricular Tachyarrhythmias by Beta-Blocker Therapy", *Clin. Cardiol.*, 20(3), (Mar. 1997),253-257.

Berger, R. D., "An Efficient Algorithm for Spectral Analysis of Heart Rate Variability", *IEEE Transactions on Biomedical Engineering*, BME-33 (9), (Sep. 1986),900-904.

Bigger, J. T., "Correlations Among Time and Frequency Domain Measures of Heart Period Variability Two Weeks After Acute Myocardial Infarction", *Arrhythmias and Conduction Disturbances*, 69, (Apr. 1, 1992),891-898.

Bigger, Jr., J. T., "Spectral Analysis of R-R Variability to Evaluate Autonomic Physiology and Pharmacology and to Predict Cardiovascular Outcomes in Humans", *Am. J. Cardiol.*, 69(9), (Apr. 2, 1992),891-898.

Bilgutay, A M., "A new concept in the treatment of hypertension utilizing an implantable electronic device: "Baropacer"", *Trans Am Soc Artif Intern Organs.*, 10, (1964),387-95.

Bilgutay, A M., "Vagal tuning for the control of supraventricular arrhythmias", *Surgical Forum*, 16, (1965),151-3.

Bilgutay, Aydin M., "Vagal tuning. A new concept in the treatment of supraventricular arrhythmias, angina pectoris, and heart failure", *Journal of Thoracic and Cardiovascular Surgery*, 56(1), (Jul. 1968),71-82.

Bocker, D. , "Ventricular Resynchronization Therapy May Restore Autonomic Balance as Evidenced by Redicung the Low Frequency to High Frequency Autonomic Ratio in Heart Failure Patients", *4th International Meeting organized by the Working Group on Heart Failure of the European Society of Cardiology (Abstract)*, Barcelona, Spain,(Jun. 11, 2001),1 p.

Borst, C , "Optimal frequency of carotid sinus nerve stimulation in treatment of angina pectoris", *Cardiovascular Research*, 8(5), (Sep. 1974),674-80.

Braunwald, E , "Carotid sinus nerve stimulation in the treatment of angina pectoris and supraventricular tachycardia", *California Medicine*, 112(3), (Mar. 1970),41-50.

Braunwald, E , "Relief of angina pectoris by electrical stimulation of the carotid-sinus nerves", *New England Journal of Medicine*, 277(24), (Dec. 14, 1967),1278-83.

Cha, Kichul , et al., "An electronic method for rapid measurement of haematocrit in blood samples", *Physiological Measurement*, 15 (2), (1994),129-137.

Cooper, T B., "Neural effects on sinus rate and atrioventricular conduction produced by electrical stimulation from a transvenous electrode catheter in the canine right pulmonary artery", *Circulation Research*, 46(1), (Jan. 1980),48-57.

Courtice, G P., "Effect of frequency and impulse pattern on the non-cholinergic cardiac response to vagal stimulation in the toad, Bufo marinus", *Journal of the Autonomic Nervous System*, 48(3), (Aug. 1994),267-72.

Crawford, Michael H., "ACC/AHA Guidelines for Ambulatory Electrocardiography", *JACC*, vol. 34, No. 3, Published by Elsevier Science Inc.,(Sep. 1999),912-948.

Dart Jr., C H., "Carotid sinus nerve stimulation treatment of angina refractory to other surgical procedures", *Annals of Thoracic Surgery*, 11(4), (Apr. 1971),348-59.

De Landsheere, D , "Effect of spinal cord stimulation on regional myocardial perfusion assessed by positron emission tomography", *American Journal of Cardiology*, 69(14), (May 1, 1992),1143-9.

Epstein, S E., "Treatment of angina pectoris by electrical stimulation of the carotid-sinus nerves", *New England Journal of Medicine*, 280(18), (May 1, 1969),971-8.

Farrehi, C , "Stimulation of the carotid sinus nerve in treatment of angina pectoris", *American Heart Journal*, 80(6), (Dec. 1970),759-65.

Feliciano, L , "Vagal nerve stimulation releases vasoactive intestinal peptide which significantly increases coronary artery blood flow", *Cardiovascular Research*, 40(1), (Oct. 1998),45-55.

Fromer, M , "Ultrarapid subthreshold stimulation for termination of atrioventricular node reentrant tachycardia", *Journal of the American College of Cardiology*, 20(4), (Oct. 1992),879-83.

Hayano, J. , "Circadian Rhythms of Atrioventricular Conduction Properties in Chronic Atrial Fibrillation With and Without Heart Failure", *JACC*, 31 (1), (Jan. 1998),pp. 158-166.

Henning, R J., "Effects of autonomic nerve stimulation, asynchrony, and load on dP/dtmax and on dP/dtmin", *American Journal of Physiology*, 260(4 Pt 2), (Apr. 1991),H1290-8.

Henning, R J., "Vagal nerve stimulation increases right ventricular contraction and relaxation and heart rate", *Cardiovascular Research*, 32(5), (Nov. 1996),846-53.

Henning, R J., "Vagal stimulation attenuates sympathetic enhancement of left ventricular function", *American Journal of Physiology*, 258(5 Pt 2), (May 1990),H1470-5.

Jessurun, G A., "Coronary blood flow dynamics during transcutaneous electrical nerve stimulation for stable angina pectoris associated with severe narrowing of one major coronary artery", *American Journal of Cardiology*, 82(8), erratum appears in Am J Cardiol Feb. 15, 1999;83(4):642,(Oct. 15, 1998),921-6.

Kadhiresan, Veerichetty, et al., U.S. Appl. No. 10/914,632, filed Aug. 9, 2004, 18 pgs.

Krig, David B., "Apparatus and Method for Treating Ventricular Tachyarrhythmias", U.S. Appl. No. 11/073,818, Filed Mar. 7, 2005, 61 pgs.

Lavery, C. E., "Nonuniform Nighttime Distribution of Acute Cardiac Events", *Circulation*, 96(10), (Nov. 18, 1997),3321-3327.

Maasrani, M. , et al., "Continuous Measurements by Impedance of Haematocrit and Plasma Volume Variations During Dialysis", *Medical & Biological Engineering & Computing*, 35 (3), (May 1997),167-171.

Mannheimer, C , "Epidural spinal electrical stimulation in severe angina pectoris", *British Heart Journal*, 59(1), (Jan. 1988),56-61.

Mannheimer, C , "Transcutaneous electrical nerve stimulation (TENS) in angina pectoris", *Pain*, 26(3), (Sep. 1986),291-300.

Mannheimer, C , "Transcutaneous electrical nerve stimulation in severe angina pectoris", *European Heart Journal*, 3(4), (Aug. 1982),297-302.

Mazgalev, T N., "Autonomic modification of the atrioventricular node during atrial fibrillation: role in the slowing of ventricular rate", *Circulation*, 99(21), (Jun. 1, 1999),2806-14.

McCabe, Aaron , "Self-Diagnostic Method and System for Implantable Cardiac Device", U.S. Appl. No. 10/890,810, Filed Jul. 14, 2004, 18 pgs.

Murphy, D F., "Intractable angina pectoris: management with dorsal column stimulation", *Medical Journal of Australia*, 146(5), (Mar. 2, 1987),260.

No Authors Listed, "Heart rate variability: standards of measurement, physiological interpretation and clinical use. Task Force of the European Society of Cardiology and the North American Society of Pacing and Electrophysiology", *Circulation*, 93(5), (Mar. 1, 1996),1043-1065.

Peckova, M. , "Circadian Variations in the Occurence of Cardiac Arrests", *Circulation*, 98(1), (1998),pp. 31-39.

Peters, T K., "Temporal and spatial summation caused by aortic nerve stimulation in rabbits. Effects of stimulation frequencies and amplitudes", *Journal of the Autonomic Nervous System*, 27(3), (Aug. 1989),193-205.

Peters, T K., "The principle of electrical carotid sinus nerve stimulation: a nerve pacemaker system for angina pectoris and hypertension therapy", *Annals of Biomedical Engineering*, 8(4-6), (1980),445-58.

Pop, G. A., et al., "Catheter-based Impedance Measurements in the Right Atrium for continuuously monitoring Hematocrit and Estimating blood Viscosity Changes; an in vivo Feasibility Study in Swine", *Biosensors and Bioelectronics*, 19 (12), (Jul. 15, 2004),1685-1693.

Schauerte, P , "Catheter stimulation of cardiac parasympathetic nerves in humans: a novel approach to the cardiac autonomic nervous system", *Circulation*, 104(20), (Nov. 13, 2001),2430-5.

Schauerte, Patrick N., et al., "Transvenous parasympathetic cardiac nerve stimulation: an approach for stable sinus rate control", *Journal of Cardiovascular Electrophysiology*, 10(11), (Nov. 1999), 1517-24.

Schauerte, Patrick N., "Transvenous Parasympathetic Nerve Stimulation in the Inferior Vena Cava and Atrioventricular Conduction", *Journal of Cardiovascular Electrophysiology*, 11(1), (Jan. 2000),64-69.

Schauerte, P , "Ventricular rate control during atrial fibrillation by cardiac parasympathetic nerve stimulation: a transvenous approach", *Journal of the American College of Cardiology*, 34(7), (Dec. 1999),2043-50.

Scherlag, M A., "Endovascular Neural Stimulation Via a Novel Basket Electrode Catheter: Comparison of Electrode Configurations", *Journal of Interventional Cardiac Electrophysiology*, 4(1), (Apr. 2000),219-224.

Smith, V. , "Systems, Devices and Methods for Tachyarrythmia Discrimination or Therapy Decisions", U.S. Appl. No. 10/897,365, Filed Jul. 22, 2004, 38 pgs.

Takahashi, N , "Vagal modulation of ventricular tacharrhythmias induced by left ansae subclaviae stimulation in rabbits", *Japanese Heart Journal*, 38(4), (Jul. 1998),503-11.

Vanoli, Emilio , "Vagal stimulation and prevention of sudden death in conscious dogs with a healed myocardial infarction", *Circulation Research*, 68(5), (May 1991),1471-81.

Wallick, D W., "Selective AV nodal vagal stimulation improves hemodynamics during acute atrial fibrillation in dogs", *American Journal of Physiology—Heart & Circulatory Physiology* , 281(4), (Oct. 2001),H1490-7.

Waninger, M S., "Electrophysiological control of ventricular rate during atrial fibrillation", *Pacing & Clinical Electrophysiology*, 23(8), (Aug. 2000),1239-44.

Yamashita, T. , "Circadian Variation of Paroxysmal Atrial Fibrillation", *Circulation*, 96 (5), (Sep. 2, 1997),pp. 1537-1541.

Zhang, Y. , et al., "Methods and Apparatuses for Arrhythmia Detection and Classification Using Wireless ECG", U.S. Appl. No. 10/975,166, filed Oct. 28, 2004, 69 Pages.

Zhang, Y , "Optimal ventricular rate slowing during atrial fibrillation by feedback AV nodal-selective vagal stimulation", *American Journal of Physiology—Heart & Circulatory Physiology*, 282(3), (Mar. 2002),H1102-10.

Zhou, X , "Prevention of high incidence of neurally mediated ventricular arrhythmias by afferent nerve stimulation in dogs", *Circulation*, 101(7), (Feb. 22, 2000),819-24.

\* cited by examiner

RESPIRATION SIGNAL MEASUREMENT APPARATUS, SYSTEMS, AND METHODS

TECHNICAL FIELD

Embodiments of the invention relate generally to biosensors and measurement apparatus, systems, and methods. More particularly, embodiments of the invention relate to measurement apparatus, systems, and methods which can be used to track the respiratory cycle, including, for example, implanted cardiac lead impedance measurement.

BACKGROUND

One task that arises during the use of cardiac rhythm management devices, including pacemakers, is that of sensing respiration. Determining the occurrence of respiration can be used to synchronously adapt pacing or defibrillation to the respiratory cycle.

The ability to operate in synchronism with a respiration signal can be used to advantage in many areas, including but not limited to respiratory sinus arrhythmia (RSA), defibrillation energy thresholds, and minute ventilation. For example, research indicates that pacing without RSA requires a higher number of beats to accomplish the same volume of oxygen delivery. Thus, proper synchronization can improve the efficiency of pulmonary gas exchange. Other research shows that synchronizing a defibrillation shock with expiration may decrease the defibrillation threshold. Finally, an improved respiration signal might provide a greater ventilation-to-cardiac component for more accurate baseline minute ventilation measurement in cases where the ventilation signal is significantly smaller than the cardiac component.

Conventional methods of sensing respiration involve measuring the impedance which arises between a ventricular lead tip electrode and an indifferent electrode on a pulse generator header. The signal obtained includes a constant component, a respiratory component, and a cardiac stroke component. The respiration component is then separated from the other components by filtering, which creates a time delay between the actual occurrence of respiration and provision of the extracted signal. The delay reduces the ability to fashion therapy according to the synchronous ideal. However, if respiratory signal quality can be improved, the need for filtering might be reduced or even eliminated, allowing cardiac therapy modification to occur in a more truly synchronous fashion.

SUMMARY

The apparatus, systems, and methods described herein provide the opportunity to detect respiration in a more reliable manner. The essence of the approach involves measuring several impedance signals, and selecting one of the signals, its correlate, or a combination of the signals and/or their correlates to provide an indication of respiration.

An exemplary apparatus according to one embodiment of the invention may include a first sensor to sense an atrial respiration signal, a second sensor to sense a ventricular respiration signal, and a measurement module coupled to the first and second sensors to monitor the atrial and ventricular respiration signals and to select a resulting signal (e.g., a combination of selected portions of the atrial and ventricular signals) as an indication of respiration.

An exemplary system according to one embodiment of the invention includes the apparatus coupled to a processor. The system may further include a current generator, an impedance measurement device, and a filter module.

An exemplary method according to an embodiment of the invention includes measuring a second signal (e.g. an atrial signal) responsive to a first signal (e.g., an injected current), measuring a third signal (e.g., a ventricular signal) responsive to the first signal, determining a respiration-to-cardiac ratio associated with each of the second and third signals, and providing a resulting signal which includes a correlate of one or both of the second and third signals (or selected portions thereof) as an indication of respiration.

This summary is intended to provide an exemplary overview of the subject matter further described hereinbelow. It is not intended to provide an exhaustive or exclusive explanation of various embodiments of the invention. The Detailed Description which follows provides further information about such embodiments.

DETAILED DESCRIPTION

Figure 1:
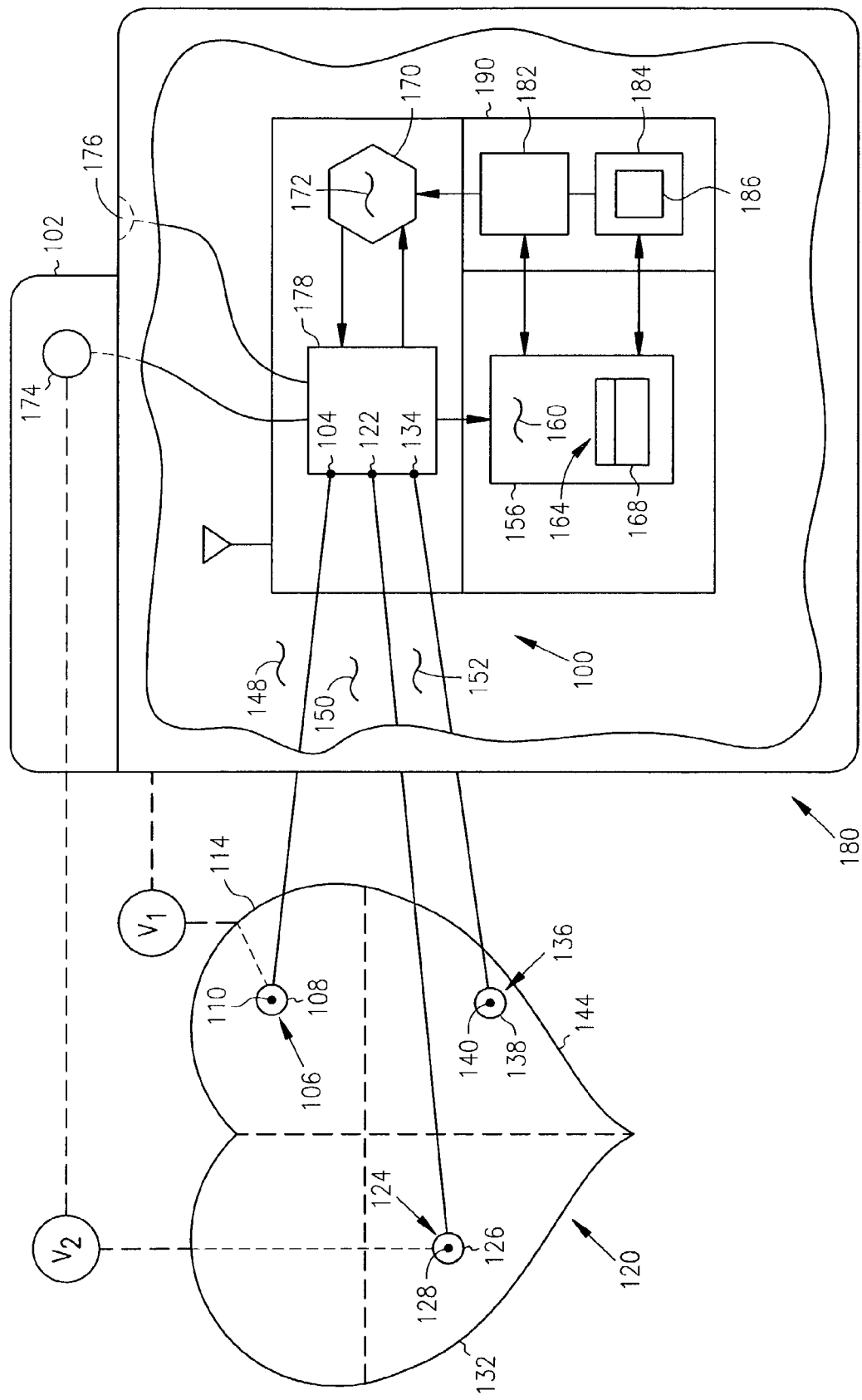
FIG. 1 is a schematic block diagram of an apparatus, and article, and a system according to various embodiments of the invention.

In the following detailed description of various embodiments of the invention, information with respect to making and using the various embodiments, including a best mode of practicing such embodiments, is provided. Thus, reference is made to the accompanying drawings which form a part hereof, and in which are shown by way of illustration, and not of limitation, specific embodiments in which the invention may be practiced. In the drawings, like numerals describe substantially similar components throughout the several views.

The embodiments illustrated are described in sufficient detail to enable those skilled in the art to practice the teachings disclosed herein. Other embodiments may be utilized and derived therefrom, such that electrical, structural, and logical substitutions and changes may be made without departing from the scope of this disclosure. The following detailed description, therefore, is not to be taken in a limiting sense, and the scope of various embodiments of the invention is defined only by the appended claims, along with the full range of equivalents to which such claims are entitled.

It is understood that the embodiments described herein may relate to ventricular and/or atrial pacing therapy. Such embodiments may be applied to mammalian hearts, human and otherwise. Embodiments include single chamber, dual chamber, tri-chamber, and quad-chamber applications. It is also understood that the apparatus, systems, and methods provided herein are not limited to implantable devices, and may be used in devices external to the body. Additionally, other devices within and without the area of cardiac rhythm management may employ aspects of the various concepts presented herein without departing from the scope of various embodiments of the invention.

An apparatus to determine the occurrence of respiration is capable of measuring a quadrapolar impedance signal using multiple electrodes (e.g. atrial ring/tip electrodes) and multiple pacer electrodes (e.g. header/can electrodes) coupled to a measurement module. By providing an alternative mechanism for impedance measurement, with a corresponding selection and/or combination of signals, the ratio of the ventilatory component to the cardiac component in the resulting respiration signal may be improved.

FIG. 1 is a schematic block diagram of an apparatus, an article, and a system according to various embodiments of the invention. The apparatus 100, which may be included in a cardiac pacer unit 102, includes one or more ports to which sensors can be attached. For example, a first port 104 may be connected to a first sensor 106 (e.g. a right atrial (RA) sensor, including an electrode pair, such as an RA ring electrode 108 and an RA tip electrode 110, disposed in the right atrium 114 of a heart 120) and a second port 122 may be connected to second sensor 124 (e.g., a left ventricular (LV) sensor, including an electrode pair, such as an LV ring electrode 126 and an LV tip electrode 128, disposed within the left ventricle 132). Other ports connected to additional sensors may also be included, such as a third port 134 connected to a third sensor 136 (e.g., a right ventricular (RV) sensor, including an electrode pair, such as an RV ring electrode 138 and an RV tip electrode 140, disposed within the right ventricle 144).

Given the exemplary sensor set illustrated in FIG. 1, the first port 104 can be used to sense an atrial respiration signal 148, and the second port 122 can be used to sense a ventricular respiration signal 150. The third port 134 may be used to sense an atrial or a ventricular respiration signal, such as a right ventricular respiration signal 152, if, for example, the second port 122 is used to sense a left ventricular respiration signal 150. Those skilled in the art, upon reading this disclosure, will realize that several other sensing arrangements are also possible.

The apparatus 100 also includes a measurement module 156 which is capable of being communicatively coupled to each of the ports 104, 122, 134, and which is used to monitor various respiration signals, such as the atrial and ventricular respiration signals 148, 150, 152, previously described. A resulting signal 160, which may include one or more of the sensed/monitored atrial and/or ventricular respiration signals 148, 150, 152, a correlate (e.g. a scaled version) of one or more of the respiration signals 148, 150, 152, or a combination of the signals 148, 150, 152, and/or their correlates, is then selected as an indication of respiration. It is also possible to select a portion of one of the signals 148, 150, 152 and combine it with a portion of another one of the signals 148, 150, 152. For example, the resulting signal 160 may include 65% of an atrial respiration signal 148 added to 32% of a ventricular respiration signal 150, 152, as well as any number of numerous other combinations.

The measurement module 156 includes an impedance measurement device 164, such as a quadrapolar impedance measurement device, capable of being communicatively coupled to the ports 104, 122, 134, as well as their corresponding sensors 106, 124, 136. The measurement module 156 may also include voltage and/or current measurement circuitry 168, such as an analog-to-digital converter, and/or a filter module 168, such as an analog or digital signal filter. The impedance measurement device 164 is capable of measuring a voltage, such as one of the voltages V1 existing between an electrode 108, 110 coupled to the first port 104 and one of the two pacer electrodes 174, 176, and a voltage existing between an electrode 126, 128 coupled to the second port 122 and one of the two pacer electrodes 174, 176.

A current injection device 170, such as a current generator, can be used to inject one or more currents 172 between any lead electrode 108, 110, 126, 128, 138, 140 and any pacer electrode, such as a header electrode 174 or a can electrode 176. One or more corresponding voltages V1, V2, arising between another lead electrode and another pacer electrode, can then be measured. Alternatively, voltages may be impressed across various combinations of electrodes, and one or more resulting currents can be measured. Thus, each sensor 106, 124, 136, such as those including the electrode pairs 108, 110, 126, 128, 138, 140, is capable of propagating a current, injected or measured, and impressing or sensing a voltage. A switch 178 may be included in the apparatus 100 and is used to control the distribution of injected currents 172, and/or impressed voltages, as well as the acquisition of the resulting signals 148, 150, 152. Thus, a single current may be injected, or a single voltage may be impressed, resulting in one or more voltages or currents, respectively, which can be sensed.

It should be noted that the respiration signals 148, 150, 152 form a part of the voltages V1, V2, and may be extracted therefrom. Thus, for example, one respiration signal 148 may be derived from a voltage V1 measured between one of the lead electrodes 108, 110 coupled to the first port 104, and one of the pacer electrodes 174, 176. Similarly, another respiration signal 150 may be derived from a voltage V2 measured between another of the lead electrodes 126, 128 coupled to the second port 122 and one of the pacer electrodes 174, 176.

It may now be easily understood that the invention also includes a system 180, including the apparatus 100 described above, as well as a processor 182 capable of being communicatively coupled to the apparatus 100. The processor 182 may also be coupled to a memory 184 containing data 186, such as program data, or data acquired via the measurement module 156. The processor 182 may be used to control various elements of the apparatus 100, such as the current injection device 170, the switch 178, and the measurement module 156.

It should be noted that current injection devices and measured voltages have been used to illustrate specific embodiments of the invention. However, other embodiments may use voltage sources, combinations of voltage and current sources, measured currents and combinations of measured voltages and currents to arrive at the same result, which is the measurement of respiration signals or other signals from which respiration signals can be reliably extracted.

The apparatus 100, the cardiac pacer unit 102, the ports 104, 122, 134, the sensors 106, 124, 136, the measurement module 156, the impedance measurement device 164, the voltage and/or current measurement circuitry 168, the filter module 168, the current injection device 170, the switch 178, the system 180, the processor 182, and the memory 184 may all be characterized as "modules" herein. Such modules may include hardware circuitry, and/or a processor and/or memory circuits, software program modules, and/or firmware, and combinations thereof, as desired by the architect of the apparatus 100 and the system 180, and as appropriate for particular implementations of various embodiments of the invention.

One of ordinary skill in the art will understand that the apparatus and systems of the present invention can be applied to systems other than those which include cardiac rhythm management devices, and thus, the invention is not to be so limited. The illustrations of an apparatus 100 and a system 180 are intended to provide a general understanding of the structure of the present invention, and they are not intended to serve as a complete description of all the elements and features of apparatus and systems that might make use of the structures described herein.

Applications that may include the novel apparatus and systems of the present invention include electronic circuitry used in communication and signal processing circuitry, modems, processor modules, embedded processors, and application-specific modules, including multilayer, multi-chip modules. Such apparatus and systems may further be utilized as sub-components within a variety of electronic systems, including cellular telephones, personal computers, radios, and others.

Figure 2:
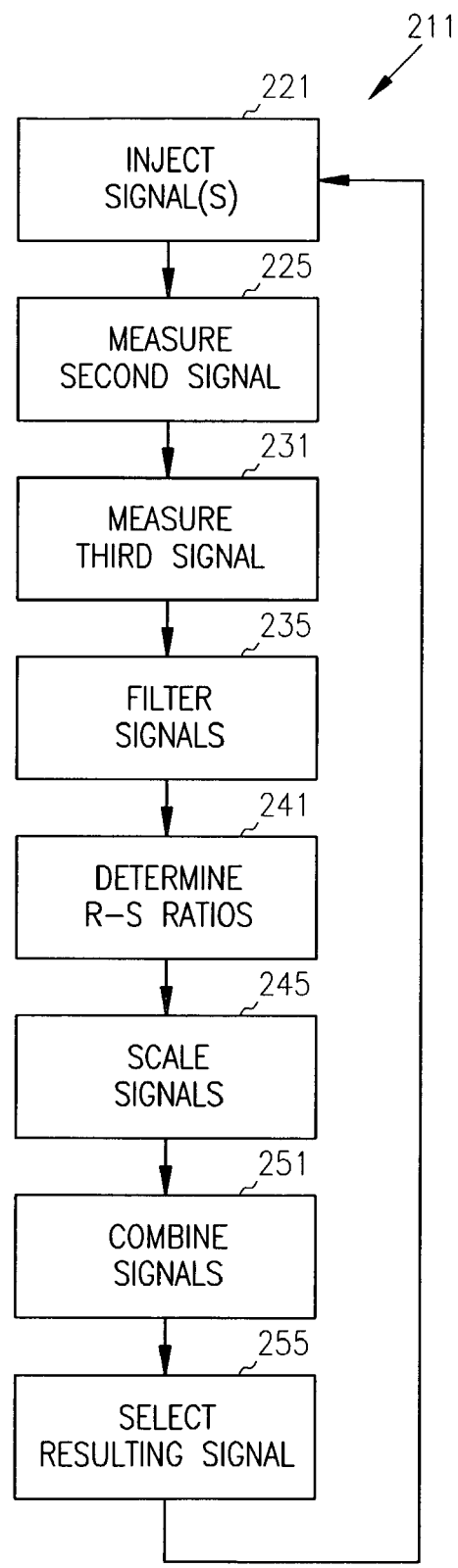
FIG. 2 is a flow diagram illustrating a method according to an embodiment of the invention.

FIG. 2 is a flow diagram illustrating a method according to an embodiment of the invention. The method 211 may begin with injecting a first signal, such as by injecting a current, or impressing a voltage, between a lead electrode, such as a tip or ring electrode, and a pacer electrode, such as a can electrode, or a header electrode, at block 221. The method may then continue with measuring a second signal (e.g., a voltage or current) responsive to the first signal at block 225, and measuring a third signal (e.g., a voltage or current) responsive to the first signal at block 231.

For example, a first signal (e.g., a current) might be injected between a right atrial ring electrode and a pacer can electrode at block 221. A corresponding voltage (e.g., a second signal, such as a voltage associated with an atrium) between the right atrial tip electrode and the pacer header electrode might then be measured at block 225. Alternatively, or in addition, a current might be injected between a left ventricular ring electrode and a pacer can electrode at block 221. A corresponding voltage (e.g., a third signal, such as a voltage associated with a ventricle) between the left ventricular tip electrode and the pacer header electrode might then be measured at block 231. Of course, multiple voltages arising from the injection of a single current pulse (e.g., the first signal) may also be measured. And, as mentioned previously, voltages may also be impressed, and the resulting currents may be measured. In any case, the measurements at blocks 225 and 231 may be repeated at various frequencies and/or times. For example, frequencies of measurement may occur within a range of about 20 times per second to about 120 times per second.

The measured signals (e.g., voltages or measured currents arising from impressed voltages) might then be filtered to extract respiratory components, if necessary, at block 235. The method may then continue with determining a respiration-to-cardiac ratio associated with each one of the second and third signals (e.g., the atrial and ventricular respiration signals) at block 241. The signals may be compared and one or the other signal might be scaled, if necessary, at block 245. Scaling may be linear, logarithmic, or by any other well-known method.

The method may then continue with combining the measured signals (e.g. the second and third signals), such as by addition or multiplication, to produce a combined signal at block 251. Alternatively, or in addition, the original of the second signal, its correlate (e.g., a scaled version), or a portion of the original second signal may be combined with an original of the third signal, its respective correlate (i.e., a scaled version), or a portion of the original third signal at block 251.

One of the measured signals, their correlates, or selected portions of the signals may be selected as the resulting signal (i.e., the signal chosen to represent the actual occurrence or indication of respiration) at block 255, depending on various parameters associated with the second and third signals. Alternatively, or in addition, the combination of the second and third signals, and/or their correlates may be selected as the resulting signal at block 255. For example, a correlate of the second signal may be selected as an indication of respiration if the respiration-to-cardiac ratio associated with the second signal is greater than the respiration-to-cardiac ratio associated with the third signal. The method may then end, or continue with the injection of signals at block 221, as described above.

Referring to the methods just described, it should be clear that some embodiments of the present invention may also be realized in the context of computer-executable instructions, such as program modules, being executed by a computer. Generally, program modules may include routines, programs, objects, components, data structures, etc. that perform particular tasks or implement particular abstract data types. As such, any of the modules 100, 102, 104, 106, 122, 124, 134, 136, 156, 164, 168, 170, 178, 180, 182, and 184 described herein may include software operative on one or more processors to perform methods according to the teachings of various embodiments of the present invention.

One of ordinary skill in the art will understand, upon reading and comprehending this disclosure, the manner in which a software program can be launched from a computer readable medium in a computer-based system to execute the functions defined in the software program. One of ordinary skill in the art will further understand the various programming languages that may be employed to create one or more software programs designed to implement and perform the methods disclosed herein. The programs can be structured in an object-orientated format using an object-oriented language such as Java, Smalltalk, or C++. Alternatively, the programs can be structured in a procedure-orientated format using a procedural language, such as COBOL or C. The software components may communicate using any of a number of mechanisms that are well-known to those skilled in the art, such as application program interfaces (API) or interprocess communication techniques such as the Remote Procedure Call (RPC). However, the teachings of various embodiments of the present invention are not limited to any particular programming language or environment.

As is evident from the preceding description, and referring back to FIG. 1, it can be seen that during the operation of the apparatus 100 a processor or control logic 182 may access some form of computer-readable media, such as the memory 184. Thus, a system 180 having an apparatus 100 according to an embodiment of the invention may also include a processor 182 coupled to a memory 184, volatile (e.g., Random Access Memory) or nonvolatile (e.g., a flash memory).

By way of example and not limitation, computer-readable media may comprise computer storage media and communications media. Computer storage media includes volatile and non-volatile, removable and non-removable media implemented in any method or technology for storage of information such as computer-readable instructions, data structures, program modules or other data. Communications media specifically embodies computer-readable instructions, data structures, program modules or other data in a modulated data signal such as a carrier wave, coded information signal, and/or other transport mechanism, which includes any information delivery media. The term "modulated data signal" means a signal that has one or more of its characteristics set or changed in such a manner as to encode information in the signal. By way of example and not limitation, communications media also includes wired media such as a wired network or direct-wired connections, and wireless media such as acoustic, optical, radio frequency, infrared and other wireless media. Combinations of any of the above are also included within the scope of computer-readable and/or accessible media.

Thus, it is now easily understood that another embodiment of the invention may include an article 190 comprising a machine-accessible medium or memory 184 having associated data 186, wherein the data 186, when accessed, results in a machine (e.g. a processor or control logic 182) performing activities such as measuring a second signal responsive to a first signal, measuring a third signal responsive to the first signal, determining a respiration-to-cardiac ratio associated with each one of the second and third signals, and providing a resulting signal including a correlate of a selected one of the second and third signals as an indication of respiration. Other activities may include combining the correlate of the selected one of the second and third signals with a correlate of the other one of the second and third signals. Alternatively, or in addition, such activities may include selecting a correlate of the second signal as an indication of respiration if the respiration-to-cardiac ratio associated with the second signal is greater than the respiration-to-cardiac ratio associated with the third signal. Further, activities may include measuring one or more voltages between an atrial tip electrode and a header electrode after injecting a current between an atrial ring electrode and a can electrode. As noted above, measuring the second signal responsive to the first signal and measuring the third signal responsive to the first signal can be repeated about 20 times per second to about 120 times per second.

Although specific embodiments have been illustrated and described herein, those of ordinary skill in the art will appreciate that any arrangement which is calculated to achieve the same purpose may be substituted for the specific embodiments shown. This disclosure is intended to cover any and all adaptations or variations of various embodiments of the present invention. It is to be understood that the above Detailed Description has been made in an illustrative fashion, and not a restrictive one. Combinations of the above embodiments, and other embodiments not specifically described herein will be apparent to those of skill in the art upon reviewing the above description. The scope of various embodiments of the invention includes any other applications in which the above structures and methods are used. Therefore, the scope of various embodiments of the invention should be determined with reference to the appended claims, along with the full range of equivalents to which such claims are entitled.

It is emphasized that the Abstract is provided to comply with 37 C.F.R. §1.72(b) requiring an abstract that will allow the reader to quickly ascertain the nature of the technical disclosure. It is submitted with the understanding that it will not be used to interpret or limit the scope or meaning of the claims. It should also be noted that in the foregoing Detailed Description, various features may be grouped together in a single embodiment for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate preferred embodiment.

What is claimed is:

1. An apparatus, comprising:
a first port to receive a first respiration signal comprising an atrial respiration signal;
a second port to receive a second respiration signal comprising a ventricular respiration signal; and
a measurement module capable of being communicatively coupled to the first and second ports to monitor the first and second respiration signals and to select a resulting signal based on the atrial and/or ventricular respiration signal as an indication of respiration.

2. The apparatus of claim 1, wherein the measurement module comprises a quadrapolar impedance measurement device capable of being communicatively coupled to the first and second ports.

3. The apparatus of claim 1, wherein the resulting signal includes a selected portion of the first respiration signal.

4. The apparatus of claim 1, wherein the resulting signal includes the first respiration signal.

5. The apparatus of claim 1, wherein the resulting signal comprises a combination of selected portions of the first and second respiration signals.

6. The apparatus of claim 1, further comprising:
a first pair of electrodes coupled to the first port, the first pair of electrodes to be disposed within an atrium; and
a second pair of electrodes coupled to the second port, the second pair of electrodes to be disposed within a ventricle.

7. The apparatus of claim 6, wherein the first and second pairs of electrodes are each capable of propagating an injected current and sensing at least one resulting voltage.

8. A system, comprising:
an apparatus, including a first port to receive a first respiration signal comprising an atrial respiration signal, a second port to receive a second respiration signal comprising a ventricular respiration signal, and a measurement module capable of being communicatively coupled to the first and second ports to monitor the first and second respiration signals and to select a resulting signal based on the atrial and/or ventricular respiration signal as an indication of respiration; and
a processor capable of being communicatively coupled to the apparatus.

9. The system of claim 8, wherein the first respiration signal is derived from a voltage measured between a first lead electrode coupled to the first port and one of two pacer electrodes.

10. The system of claim 9, wherein the second respiration signal is derived from a voltage measured between a second lead electrode coupled to the second port and one of the two pacer electrodes.

11. The system of claim 8, further comprising a current injection device capable of being communicatively coupled to the processor.

12. The system of claim 8, further comprising a filter module capable of being communicatively coupled to the measurement module.

13. The system of claim 8, further comprising:
a quadrapolar impedance measurement device included in the measurement module, the quadrapolar measurement device capable of measuring a voltage existing between an electrode coupled to the first port and one of two pacer electrodes, and a voltage existing between an electrode coupled to the second port and one of the two pacer electrodes.

14. The system of claim 13, wherein the resulting signal comprises a selected portion of the atrial respiration signal added to a selected portion of the ventricular respiration signal.

15. A method, comprising:
measuring a second signal responsive to a first signal;
measuring a third signal responsive to the first signal;
determining a respiration-to-cardiac ratio associated with each one of the second and third signals; and
providing a resulting signal including a correlate of a selected one of the second and third signals as an indication of respiration.

16. The method of claim 15, wherein measuring a second signal responsive to the first signal includes measuring a voltage associated with a ventricle.

17. The method of claim 16, wherein measuring a third signal responsive to the first signal includes measuring a voltage associated with an atrium.

18. The method of claim 15, wherein the first signal is a current.

19. The method of claim 18, comprising:
 injecting the first signal between a lead electrode and a can electrode.

20. An article comprising a machine-accessible medium having associated data, wherein the data, when accessed by a machine, results in the machine performing:
 measuring a second signal responsive to a first signal;
 measuring a third signal responsive to the first signal;
 determining a respiration-to-cardiac ratio associated with each one of the second and third signals; and
 providing a resulting signal including a selected portion of a selected one of the second and third signals as an indication of respiration.

21. The article of claim 20, wherein providing a resulting signal including a selected portion of a selected one of the second and third signals as an indication of respiration comprises:
 combining the selected portion of the selected one of the second and third signals with a correlate of the other one of the second and third signals.

22. The article of claim 20, wherein providing a resulting signal including a selected portion of a selected one of the second and third signals as an indication of respiration comprises:
 selecting a correlate of the second signal as an indication of respiration if the respiration-to-cardiac ratio associated with the second signal is greater than the respiration-to-cardiac ratio associated with the third signal.

23. The article of claim 20, wherein measuring the second signal responsive to the first signal and measuring the third signal responsive to the first signal comprise:
 measuring a voltage between an atrial tip electrode and a header electrode after injecting a current between an atrial ring electrode and a can electrode.

24. The article of claim 20, wherein measuring the second signal responsive to the first signal and measuring the third signal responsive to the first signal are each repeated about 20 times per second to about 120 times per second.

* * * * *